United States Patent
Davenport et al.

(10) Patent No.: US 10,653,482 B2
(45) Date of Patent: May 19, 2020

(54) SYSTEM FOR VAPORIZATION OF TISSUE

(71) Applicant: Boston Scientific Scimed, Inc., Maple Grove, MN (US)

(72) Inventors: Scott A. Davenport, Half Moon Bay, CA (US); Steven G. Murray; Tony D. Coleman, San Jose, CA (US); Henry Garlich, Cameron Park, CA (US); Kenneth J. Arnold, Corralitos, CA (US); Kester Nahen, Heidelberg (DE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1761 days.

(21) Appl. No.: 14/157,410

(22) Filed: Jan. 16, 2014

(65) Prior Publication Data

US 2014/0221989 A1 Aug. 7, 2014

Related U.S. Application Data

(63) Continuation of application No. 12/145,370, filed on Jun. 24, 2008, now abandoned, which is a
(Continued)

(51) Int. Cl.
*A61B 18/20* (2006.01)
*A61B 18/22* (2006.01)
(Continued)

(52) U.S. Cl.
CPC .............. *A61B 18/20* (2013.01); *A61B 18/22* (2013.01); *A61B 2017/00274* (2013.01);
(Continued)

(58) Field of Classification Search
CPC .................... A61B 18/20; A61B 18/22; A61B 2017/00274; A61B 2018/00547;
(Continued)

(56) References Cited

U.S. PATENT DOCUMENTS 4,383,318 A 5/1983 Barry et al.
4,402,569 A 9/1983 Bow et al.
(Continued)

FOREIGN PATENT DOCUMENTS

WO 96/28998 9/1996
WO 97/15226 5/1997
WO 98/32381 7/1998

OTHER PUBLICATIONS

Kuntzman et al, "High Power (60-Watt) Potassiun-tytanyl-phosphate laser vaporization prostatectomy in living canines and in human and canine cadavers", Urology, vol. 48, 1997, pp. 703-708.*
(Continued)

*Primary Examiner* — Catherine M Voorhees
(74) *Attorney, Agent, or Firm* — Bookoff McAndrews, PLLC

(57) ABSTRACT

A method for photoselective vaporization of prostate tissue includes delivering laser radiation to the treatment area on the tissue, via an optical fiber for example, wherein the laser radiation has a wavelength and irradiance in the treatment area on the surface of the tissue sufficient because vaporization of a substantially greater volume of tissue than a volume of residual coagulated tissue caused by the laser radiation. The laser radiation is generated using a neodymium doped solid-state laser, including optics producing a second or higher harmonic output with greater than 60 watts average output power. The delivered laser radiation has a wavelength for example in a range of about 200 nm to about 650 nm, and has an average irradiance in the treatment area greater than about 10 kilowatts/cm$^2$, in a spot size of at least 0.05 mm$^2$.

19 Claims, 8 Drawing Sheets

Related U.S. Application Data continuation of application No. 11/191,197, filed on Jul. 27, 2005, now abandoned, which is a continuation of application No. 10/278,723, filed on Oct. 23, 2002, now Pat. No. 6,986,764, which is a continuation-in-part of application No. 09/737,721, filed on Dec. 15, 2000, now Pat. No. 6,554,824.

(60) Provisional application No. 60/337,810, filed on Nov. 5, 2001, provisional application No. 60/338,728, filed on Nov. 5, 2001, provisional application No. 60/336,481, filed on Oct. 24, 2001.

(51) Int. Cl.
*A61B 18/00* (2006.01)
*A61B 17/00* (2006.01)

(52) U.S. Cl.
CPC .............. *A61B 2018/00547* (2013.01); *A61B 2018/00625* (2013.01); *A61B 2018/00982* (2013.01); *A61B 2018/2015* (2013.01); *A61B 2018/2272* (2013.01)

(58) Field of Classification Search
CPC .... A61B 2018/2015; A61B 2018/2272; A61B 2018/00625; A61B 2018/00982
USPC .................................................. 606/3, 10–18
See application file for complete search history.

(56) References Cited

U.S. PATENT DOCUMENTS

| | | | |
|---|---|---|---|
| 4,418,689 A | | 12/1983 | Kanazawa et al. |
| 4,646,737 A | | 3/1987 | Hussein et al. |
| 4,648,892 A | | 3/1987 | Kittrell et al. |
| 4,722,337 A | | 2/1988 | Losch et al. |
| 4,760,840 A | | 8/1988 | Fournier, Jr. et al. |
| 4,784,135 A | | 11/1988 | Blum et al. |
| 4,802,461 A | | 2/1989 | Cho |
| 4,834,091 A | | 5/1989 | Ott |
| 4,836,189 A | | 6/1989 | Allred, III et al. |
| 4,862,886 A | * | 9/1989 | Clarke ................. A61B 18/245 606/7 |
| 4,907,235 A | * | 3/1990 | Kuizenga ................ H01S 3/109 359/328 |
| 4,944,738 A | | 7/1990 | Rodriguez |
| 4,981,138 A | | 1/1991 | Deckelbaum et al. |
| 5,025,446 A | | 6/1991 | Kuizenga |
| 5,066,291 A | | 11/1991 | Stewart |
| 5,071,422 A | | 12/1991 | Watson et al. |
| 5,147,353 A | | 9/1992 | Everett |
| 5,151,909 A | | 9/1992 | Davenport et al. |
| 5,231,641 A | | 7/1993 | Ortiz |
| 5,242,390 A | | 9/1993 | Goldrath |
| 5,242,437 A | | 9/1993 | Everett et al. |
| 5,243,615 A | * | 9/1993 | Ortiz .................... H01S 3/093 372/21 |
| 5,249,192 A | | 9/1993 | Kuizenga et al. |
| 5,257,991 A | | 11/1993 | Fletcher et al. |
| 5,269,779 A | | 12/1993 | Sogawa et al. |
| 5,300,061 A | | 4/1994 | Easley et al. |
| 5,312,392 A | | 5/1994 | Hofstetter et al. |
| 5,312,396 A | | 5/1994 | Feld et al. |
| 5,380,317 A | | 1/1995 | Everett et al. |
| 5,409,481 A | | 4/1995 | Poppas et al. |
| 5,409,483 A | | 4/1995 | Campbell et al. |
| 5,421,323 A | | 6/1995 | Herrmann et al. |
| 5,428,699 A | | 6/1995 | Pon |
| 5,437,660 A | * | 8/1995 | Johnson ................. A61B 18/24 606/15 |
| 5,449,354 A | | 9/1995 | Konwitz et al. |
| 5,451,221 A | | 9/1995 | Cho et al. |
| 5,487,740 A | | 1/1996 | Sulek et al. |
| 5,495,541 A | * | 2/1996 | Murray .................. A61B 18/24 385/117 |
| 5,520,679 A | | 5/1996 | Lin |
| 5,542,944 A | | 8/1996 | Bhatta |
| 5,593,404 A | | 1/1997 | Costello et al. |
| 5,599,349 A | | 2/1997 | D'Amelio |
| 5,607,420 A | | 3/1997 | Schuman |
| 5,628,744 A | | 5/1997 | Coleman et al. |
| 5,632,739 A | | 5/1997 | Anderson et al. |
| 5,649,924 A | | 7/1997 | Everett et al. |
| 5,662,646 A | | 9/1997 | Fumich |
| 5,700,260 A | | 12/1997 | Cho et al. |
| 5,733,279 A | | 3/1998 | Konwitz et al. |
| 5,746,760 A | | 5/1998 | Humphrey, Jr. |
| 5,772,658 A | | 6/1998 | Konwitz et al. |
| 5,776,127 A | | 7/1998 | Anderson et al. |
| 5,776,175 A | | 7/1998 | Eckhouse et al. |
| 5,778,395 A | | 7/1998 | Whiting et al. |
| 5,798,518 A | | 8/1998 | Coleman et al. |
| 5,807,389 A | | 9/1998 | Gardetto et al. |
| 5,841,800 A | | 11/1998 | Davenport et al. |
| 5,843,026 A | | 12/1998 | Edwards et al. |
| 6,016,324 A | * | 1/2000 | Rieger ..................... H01S 3/117 372/10 |
| 6,024,751 A | | 2/2000 | Lovato et al. |
| 6,033,400 A | | 3/2000 | Grossi et al. |
| 6,055,458 A | * | 4/2000 | Cochran ............. A61F 9/00736 604/65 |
| 6,064,914 A | | 5/2000 | Trachtenberg et al. |
| 6,086,580 A | | 7/2000 | Mordon et al. |
| 6,112,747 A | | 9/2000 | Jones et al. |
| 6,156,030 A | | 12/2000 | Neev |
| 6,197,025 B1 | | 3/2001 | Grossi et al. |
| 6,389,313 B1 | | 5/2002 | Marchitto et al. |
| 6,423,055 B1 | | 7/2002 | Farr et al. |
| 6,482,199 B1 | | 11/2002 | Neev |
| 6,530,921 B1 | | 3/2003 | Maki et al. |
| 6,554,824 B2 | | 4/2003 | Davenport et al. |
| 6,554,825 B1 | | 4/2003 | Murray et al. |
| 6,596,017 B1 | | 7/2003 | Bolmsjo et al. |
| 6,699,239 B1 | | 3/2004 | Stiller et al. |
| 6,701,044 B2 | * | 3/2004 | Arbore .................... H01S 3/113 385/37 |
| 6,986,764 B2 | | 1/2006 | Davenport et al. |
| 2002/0108937 A1 | * | 8/2002 | Shapovalov ....... B23K 26/0643 219/121.72 |
| 2002/0162973 A1 | * | 11/2002 | Cordingley .......... B23K 26/032 250/492.2 |
| 2002/0193850 A1 | | 12/2002 | Selman |

OTHER PUBLICATIONS

Barber et al, "High-power KTP laser prostatectomy—the new challenge to transurethral resection of the prostate", Current Opinions in Urology, vol. 14, 2004, pp. 21-25.*

Dixon, J.A., "Argon and Neodymium YAG Laser Therapy of Dark Nodular Port Wine Statins in Older Patients," Lasers in Surgery and Medicine 6:5-11 (1986).

Grabo, Theresa N., et al., "Uterine Myomas: Treatment Options," JOGNN 28(1) (Jan./Feb. 1999), 23-31.

Indman, Paul D., et al., "Uterine Surface Temperature Changes Caused by Endometrial Treatment with the Nd:YAG Laser," J Reprod Med 36(7) (Jul. 1991), 505-512.

Narayan, P., et al., "Transurethral Evaporation of the Prostate for Treatment of Benign Prostatic Hyperplasia: Results in 168 Patients with up to 12 Months of Followup," The Journal of Urology, vol. 157(4), Apr. 1997, 7 pages.

Reply to Counterclaims Civil Action No. 3:07-cv-30109-MAP (Aug. 10, 2007) *American Medical Systems, Inc. and Laserscope v. Biolitec, Inc.* 3 pages.

Rosenfeld, Harold, et al., "Treatment of Cutaneous and Deep Vascular Lesions with the Nd:YAG Laser," Lasers in Surgery and Medicine, vol. 6, pp. 20-23, 1986.

Schneider, Ellen Meyer, "Try Different Lasers for Treating Blood Vessel Disorders," Cosmetic Surgery Times, Oct. 1999.

(56) References Cited

OTHER PUBLICATIONS

Stein, B., "Neodymium: Yttrium-Aluminum-Garnet Laser Prostatectomy," Mayo Clin Proc 1998; 73:787-791 (6 pages) http://www.mayoclinicproceedings.com/inside/asp?AID=3012&UID=.
Svelto, Orazio, "Principles of Lasers," Fourth Ed., pp. 480-482, Plenum Press, New York, NY, 1998.
Van Gemert, Martin J.C., Ph.D., et al., "Is There an Optimal Laser Treatment for Port Wine Stains?" Lsers in Surgery and Medicine, vol. 6, pp. 76-83, Alan R. Liss, Inc., 1986.
Van Gemert, Martin J.C., Ph.D., et al., "Treatment of Port-Wine Stains: Analysis" Medical Instrumentation, vol. 21, No. 4, pp. 213-217, Association for the Advancement of Medical Instrumentation, 1987.
Van Swol, Christiaan F.P., et al., "Physical Evaluation of Laser Prostatectomy Devices," Lasers in Urology, Eds. Watson GM, Steiner RW and Johnson DE, SPIE Bellingham, vol. 2129, 1994.
Zelickson, Brian D., M.D., et al., "Preliminary Results of the Lyra Long Pulsed Nd:YAG Laser Treatement of Leg Veins," Abstract of the Presentation by Dr. brian Zelickson at the ISCLS in May 2000.
"Laserscope Accounces FDA Clearance for Pseudo-Folliculitis," Laserscope.com/news/021401htm, Feb. 14, 2001, pp. 1-2.
"Laserscope Announces a Winner of the Palm Pilot Drawing," Laserscope.com/news/100300.htm, Sep. 29, 2000, p. 1.
"Laserscope Announces Approvable Letter Received for PDT Laser System for the Treatment of Head and Neck Cancer," Laserscope.com/news/052200.htm, May 22, 2000, pp. 102.
"Laserscope Announces High Power Lyra Laser System: Lyra XP, AAD to be Introduced at the ADD," Laserscope.com/news/030800.htm, Mar. 8, 2000, pp. 1-2.
"Laserscope Encouraged by Clinical Study Using New Lyra Laser System to Treat Leg Veins,". Laserscope.com/news/120799.htm, Dec. 7, 1999, pp. 1-2.
"Laserscope Receives FDA Clearnace ot Market New LYRA Laser System for Hair Removal: First laser Designed for Full Range of Skin Types," Laserscope.com/new/031300.htm, Mar. 13, 2000.
"Laserscope Reports First Quarter 2000 Results," Laserscope.com/news/050400.htm, May 4, 2000, pp. 103.
"Laserscope Reports Fourth Quarter and Year End 2000 Results," Laserscope.com/news/021301.htm, Feb. 13, 2001, pp. 1-3.
"Laserscope Reports Increased Profits in Third Quarter 2000 Results" Laserscope.com/news/101900.htm, Oct. 19, 2000, pp. 1-3.
"Laserscope Signs Exclusive Agreement with McKessonHBOC Medical Group for National Distribution of Aesthetic Laser Systems," Laserscope.com/news/121400.htm, Dec. 14, 2000, pp. 1-2.
"Researchers Report Decidedly Positive Two-Year Results Using Laserscope's Ultra High Power Laser and Disposable Fiber Optics to Treat BPH: Researchers Call the Results Unprecedented,", Laserscope.com/news/060800.htm, Jun. 8, 2000, pp. 1-2.
"The Lyra Laser System from Laserscope Long-pulse Nd:YAG Laser Proven in Cosmetic Treatments," Medco Forum, vol. 7. No. 2, Mar. 2000.
Answer to Complaint in Civil Action 3:07-cv-30109-MAP, *Americal Medical Systems, Inc. and Laserscope v. Biolitec, Inc.* (Jul. 18, 2007) 8 pages.
Buttram, Veasy C., et al., "Indications for Myomectomy," Seminars in Reproductive Endocrinology 10(4) (Nov. 1992) 378-384.
Chui, Carie T., M.D., et al., "Long-Pulsed Nd:YAG for Hair Removal: Early Histological Changes," LaserNews.net, LLC, 1999.
Complaint in Civil Action 07-30109MAP, *American Medical Systems, Inc. and Laserscope v. Biolitec, Inc.* (Jun. 14, 2007) 31 pages.
Conford, P.A., et al., "Transurethral Incision of the Prostate Using the Holmium: YAG Laser: a Catheterless Procedure," The Journal of Urology, vol. 159, Apr. 1998, pp. 1229-1231, American Urological Association, Inc.
Dixon, J.A., "Argon and Neodymium YAG Laser Therapy of Dark Nodular Port Wine Stains in Older Patients," Lasers in Surgery and Medicine 6:5-11 (1986).
Gilling, Peter, "Holmium Laser Resection of the Prostate Versus Neodymium:Yttrium-Aluminum-Garnet Visual Laser Ablation of the Prostate: Randomized Prospective Comparison of Two Techniques for Laser Prostatectomy," Urology, vol. 51, No. 2, pp. 254-256, Elsevier Science, Inc., 1998.

Gilling, Peter, J., el al., "Combination Holmium and Nd:YAG Laser Ablation of the Prostate: Initial Clinical Experience," Journal of Endourology, vol. 9, No. 2, Apr. 1995, Mary Ann Liebert, Inc., Publishers.
Gilling, Peter, J., et al., "Holmium Laser Versus Transurethral Resection of the Prostate: a Randomized Prospective Trial with 1-Year Followup," The Journal of Urology, vol. 162, Nov. 1999, pp. 1640-1644, American Urological Association.
Grabo, Theresa N., et al., "Uterine Myomas: Treatment Options," JOGNN 26(1) (Jan./Feb. 1999), 23-31.
Hai, Mahmood A., M.D., et al., "Photoselective Vaporization of the Prostate in Treatment of Symptomatic Benign Prostatic Hyperplasia: Initial Experience," Abstract, Dept of Urology, Oakwood Annapolis Medical Center, Detroit, MI. 2001 Laserscope, www.laserscope.com.
In re Sarett, No. 7051, Unites States Court of Customs and Patent Appeals, 51 C.C.P.A. 1180 327 F.2d 1005; 1964 CCPA Lexis 475; 140U.S.P.Q. (BNA) 474.
In re Virgil W. Vogel and Paul W. Vogel, No. 8198, United States Court of Customs and Patent Appeals, 57 C.C.P.A. 920; 422 F.2d 438;1970 CCPA Lexis 423;164 U.S.P.Q. (BNA) 619.
Indman, Paul D., "High-Power Nd:YAG Laser Ablation of the Endometrium," J Repro Med 36(7) (Jul. 1991), 501-504.
Indman, Paul D., "Hysteroscopic Treatment of Menorrhagia Associated with Uterine Leiomyomas," Obstetrics & Gynecology 81(5) part 1 (May 1993), 716-720.
Inuman, Paul D., et al., "Uterine Surface Temperature Changes Caused by Endometial Treatment with the Nd:YAG Laser," J Reprod Med 36(7) (Jul. 1991), 505-512.
Jacques, Steven L., PhD., "Laser-Tissue Interactions, Photochemical, Photothermal, and Photomechanical" Lasers in General Surgery, vol. 72, No. 3, Jun. 1992, 531-558.
Kollmorgen, Thomas A., et al., "Laser Prostatectomy: Two and a Half Years' Experience with Aggressive Multifocal Therapy," Urology, 48(2) 1996 217-222.
Kuntzman, Randall S., et al., "High-Power (60-Watt) Potassium-Titanyl-Phosphate Laser Vaporiztion Prostatectomy in Living Canines and in Human and Canine Cadavers," Urology, 49(5), pp. 703-708, Elsevier Science, Inc. 1997.
Kuntzman, Randall S., et al., "High-Power Potassium Titanyl Phosphate Laser Vaporization Prostatectomy," Mayo Clin Prac, 1998:73:798-801.
Kuntzman, Randall S., et al., "Potassium-Titanyl-Phosphate Laser Vaporization of the Prostate: A Comparative Functional and Pathologic Study in Canines," Urology 48(4) 1996 575-583.
Lahaye, C.T.W., et al., "Optimal Laser Parameters for Port Wine Stain Therapy: A Theoretical Approach," Phys. Med. Biol., vol. 30, No. 6, pp. 573-587, 1985.
Langhaler, M., M.D., et al., "Effects of Argon, Dye, and Nd:YAG Lasers on Epidermis, Dermis, and Venous Vessels," Lasers in Surgery and Medicine, vol. 6, pp. 87-93, Alan R. Liss, Inc., 1986.
Laserscope Announces PMA Application to U.S. Food and Drug Administration for PDT Treatment of Head and Neck Cancer, Laserscope.com/news/110999.htm, Nov. 9, 1999, pp. 1-2.
Le Duc, A., et al., "Holmium Laser Resection of teh Prostate," Eur Urol 1999: 35: 155-160.
Malek, Reza S., et al., "High Power Potassium-Titanyl-Phosphate Laser Vaporization Prostatectomy," The Journal of Urology, vol. 163, Jun. 2000, pp. 1730-1733, American Urological Association, Inc.
Malek, Reza S., et al., "High-Power Potassium-Titanyl-Phosphate (KTP/532) Laser Vaporization Prostatectomy: 24 Hours Later," Urology, 51(2) pp. 254-256, Elsevier Science, Inc., 1998.
Malek, Reza S., et al., "KTP Laser Prostatectomy: Long-term Experience," can be found at www.laserscope.com.
Mansell et al., "Evaluating the effect of transmissive optic thermal lensing on laser beam quality with a Shack-Hartmann wave-front sensor," Applied Optics, vol. 40, No. 3, Jan. 20, 2001, pp. 366-374.
Moretti, Michael, "Laserscope's Lyra Laser Proves Multi-Functional," Aesthetic Buyers Guide, Medical Insight Inc., Jul. 2000.

(56) References Cited

OTHER PUBLICATIONS

Mottet, Nicolas, M.D., Ph.D., et al., "Randomized Comparison of Transurethral Electroresection and Holmium: YAG Laser Vaporization for Symptomatic Benign Prostatic Hyperplasia," Journal of Endourology, vol. 13, No. 2, Mar. 1999, pp. 127-130, Mary Ann Liebert, Inc.

Narayan, P., et al., "Transurethral Evaporation of the Prostate for Treatment of Benign Prostate Hyperplasia: Results in 168 Patients with up to 12 Months of Followup" The Journal of Urology, vol. 157(4), Apr. 1997, 7 pages.

Reply to Counterclaims Civil Action No. 3:07-cv-30189-MAP (Aug. 10, 2007) *American Medical Systems, Inc. and Laserscope* v. *Biolitec, Inc.* 3 pages.

*Rosco, Inc.* v. *Mirror Lite Company*, United States Court of Appeals for the Federal Circuit, 01-1271, -1302 2002.

\* cited by examiner

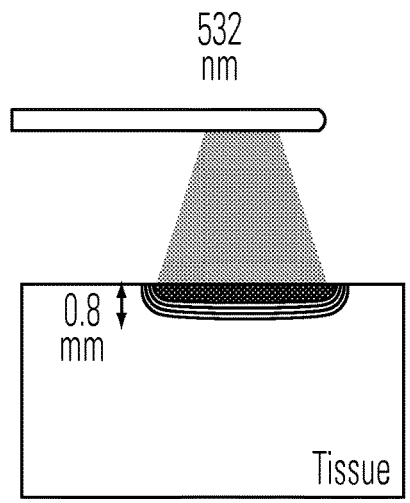
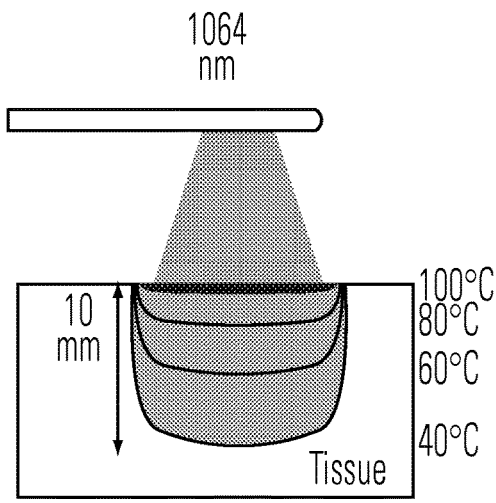
FIG. 8  FIG. 9
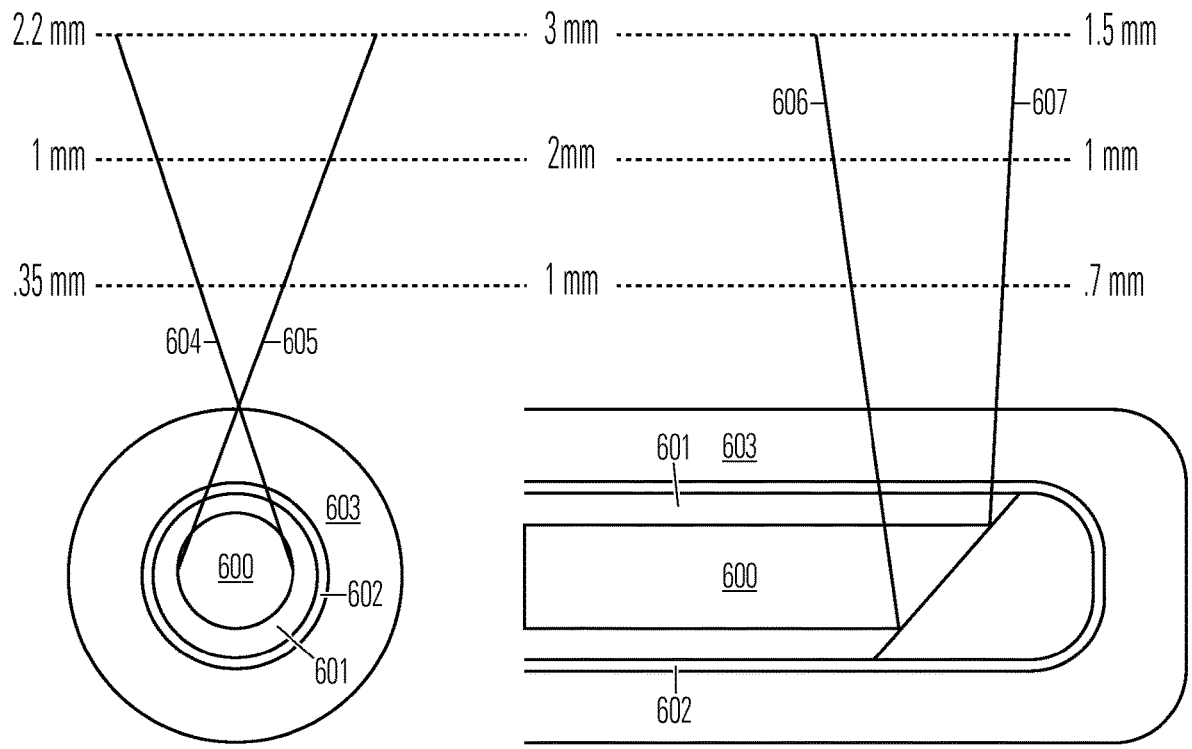
FIG. 10  FIG. 11

SYSTEM FOR VAPORIZATION OF TISSUE

RELATED AND CONTINUING APPLICATION INFORMATION

This application is a continuation of U.S. patent application Ser. No. 12/145,370 filed on 24 Jun. 2008 (now abandoned).

Application Ser. No. 12/145,370 is a continuation of U.S. patent application Ser. No. 11/191,197 filed on 27 Jul. 2005 (now abandoned).

Application Ser. No. 11/191,197 is a continuation of application Ser. No. 10/278,723 filed on 23 Oct. 2002 (now U.S. Pat. No. 6,986,764).

Application Ser. No. 10/278,723 is a continuation-in-part of U.S. patent application Ser. No. 09/737,721 (U.S. Pat. No. 6,554,824).

Application Ser. No. 10/278,723 also claims the benefit of U.S. Provisional Application No. 60/336,481, filed 24 Oct. 2001.

Application Ser. No. 10/278,723 also claims the benefit of U.S. Provisional Application No. 60/338,728, filed 5 Nov. 2001; and Application Ser. No. 10/278,723 also claims the benefit of U.S. Provisional Application No. 60/337,810, filed 5 Nov. 2001.

The present application is related to U.S. patent application Ser. No. 10/279,087 filed on 23 Oct. 2002 (now abandoned).

BACKGROUND OF THE INVENTION

Field of the Invention

The present invention relates generally to laser treatment of soft tissue, and more particularly to photoselective vaporization of the prostate PVP, and to photoselective vaporization of other tissue.

Description of Related Art

Benign Prostatic Hyperplasia (BPH) is a condition wherein continued growth of the prostate restricts the passage of urine through the lower portion of the bladder and the urethra. BPH is often treated by surgically removing excess prostate tissue from the transitional zone of the prostate that is pressing on the urethra, which usually relieves the bladder outlet obstruction and incomplete emptying of the bladder caused by the BPH.

Recently, the most commonly employed procedure for removal of excess prostate tissue has been transurethral resection of the prostate, also known as TURP. In the TURP procedure, the surgeon utilizes a standard electrical cutting loop to shave off small pieces of the targeted tissue from the interior of the prostate. At the end of the operation, pieces of excised prostate tissue are flushed out of the bladder using an irrigant.

While effective, the TURP procedure is known to cause numerous side effects, including incontinence, impotence, retrograde ejaculation, prolonged bleeding and TUR syndrome. Recently, alternative procedures have been developed which reduce or avoid the side effects associated with TURP. One class of procedures involves "cooking" prostate tissue by heating it to a to a temperature above 45 degrees Celsius, causing tissue coagulation. Typically this is accomplished using electrically resistive elements such as: radio frequency (RF), microwave, or long-wavelength lasers. An example of a procedure of this nature is discussed in U.S. Pat. No. 6,064,914 by Trachtenberg ("Thermotherapy Method"). Because these procedures leave the thermally-treated tissue in place, post-procedure edema, dysuria, and retention rates are relatively high. Further, use of thermal procedures requires the patient to be catheterized for several days following the procedure, and may cause extensive and unpredictable scarring of the intra prostatic urethra.

Another class of procedures involves vaporizing or ablating the targeted tissue using laser light. These procedures generally avoid the high infection rates and scarring problems of thermally-based procedures. However, laser ablation of prostate tissue has to date, required the use of an expensive laser capable of generating high-power laser light. The high cost of purchasing or leasing such a laser results in a concomitant increase in the cost of the procedure. Finally, the ablation process typically occurs slowly, resulting in a lengthy procedure time.

The Ho:YAG laser and its fiberoptic delivery system is an example of a laser that is commonly used for ablating prostate tissue. The Ho:YAG laser generates pulses of 2100 nm light that are strongly absorbed by water in the prostate tissue and in the saline irrigant positioned between the distal end if the fiberoptic and the tissue. The absorption coefficient of water is so high at 2100 nm that 50% of the light is absorbed within 0.2 mm of water. Consequently even a thin layer of irrigant positioned between the distal end on the fiberoptic and the tissue will absorb a large fraction of the laser light. Furthermore with the short pulse durations (Tp<0.5 ms) and large pulse energies (Ep>1.0 joule) used for ablating prostate tissue the irrigant is explosively boiled creating a shock wave that tears tissue. Because water is such a large constituent of prostate tissue and blood, there is essentially no selective absorption by blood. This combination of violent tissue disruption and the superficial unselective light penetration leads to poor hemostasis.

Nd:YAG lasers operating at 1064 nm have also been used for ablating prostate tissue. Although 1064 nm light is hemostatic at high power levels its low absorption in blood and prostate tissue leads to inefficient ablation and a large residual layer of thermally denatured tissue several millimeters thick. After surgery, the coagulated, thermally denatured tissue swells and leads to transient urinary retention, which can cause long catheterization times, painful urination, and high infection rates.

Frequency doubled Nd:YAG lasers operating at 532 nm in a Quasi continuous mode at power levels up to 60 watts have been used to efficiently and hemostatically ablate prostate tissue. These lasers are pumped by CW krypton arc lamps and produce a constant train of Q-switched pulses at 25 kHz. The high Q-Switch frequency makes the tissue effects indistinguishable from CW lasers of the same average power. The 532 nm light from these lasers is selectively absorbed by blood leading to good hemostasis. When ablative power densities are used, a superficial layer of denatured prostate tissue less than 1 mm is left behind. This thin layer of denatured tissue is thin enough that the immediate post surgical swelling associated with other treatment modalities is greatly reduced. This reduced swelling leads to short catheterization times and less dysuria. At high powers, 532 nm lasers induce a superficial char layer (an absorptive, denatured layer) that strongly absorbs the laser light and greatly improves the ablation efficiency. The problem with the existing 532 nm lasers used to date is that they are large, expensive, inefficient, and have a highly multi-mode output beam that makes them inefficient for ablating prostate tissue.

Furthermore, residual coagulation of tissue due to the procedure remains significant using the techniques known in the prior art, as discussed below.

High power densities are required for rapid and efficient vaporization of prostate tissue. The difficulty of achieving higher average output power densities is that when high input powers are supplied to the laser element from an excitation source such as an arclamp a large amount of heat is generated in the lasing element. This heat induces various deleterious effects in the lasing element. In particular the temperature difference between the coolant and the hot lasing element generates a thermally induced graded index lens that decreases the beam quality of the laser and causes the laser to operate with more transverse optical modes than it would otherwise.

The $M^2$ parameter is a well established convention for defining the beam quality of a laser and is discussed in pages 480-482 of Orazio Svelto and David C. Hanna, *Principles of Lasers*, Plenum Press, New York, 1998, which is incorporated herein by reference. The beam quality measures the degree to which the intensity distribution is Gaussian. The quantity $M^2$ is sometimes called inverse beam quality rather than beam quality but in this application it will be referred to as beam quality. $M^2$ is defined as $$M_x^2 \equiv \frac{(\sigma_x \sigma_f)_{NG}}{(\sigma_x \sigma_f)_G} = 4\pi(\sigma_x \sigma_f)_{NG},$$

where $\pi$ refers to the number 3.14 . . . , $\sigma$ is used to represent the spot size, the subscripts x and f represent the spatial and frequency domains along the x-axis, respectively, and the subscripts G and NG signify Gaussian and non-Gaussian, respectively. The x-axis is transverse to the direction of propagation of the beam. The beam quality in any direction transverse to the beam may be essentially the same. Therefore the subscript x is dropped from the $M^2$ elsewhere in the specification. The beam widths or σs are determined based on the standard deviation of the position, where the squared deviation of each position is weighted by the intensity at that point. The beam width in the frequency domain $\sigma_f$ is the beam width of the beam after being Fourier transformed.

The formula usually used for calculating the angular divergence, $\theta$, of a beam of light of wavelength $\lambda$ is strictly valid only for a beam having a Gaussian intensity distribution. The concept of beam quality facilitates the derivation of the angular divergence, $\theta$, for the beam with a non-Gaussian intensity distribution, according to $$\theta = M^2\left(\frac{2\lambda}{\pi\sigma_x}\right).$$

For example, a TEM00 laser beam has a high beam quality with an $M^2$ of 1, whereas by comparison, high power surgical lasers operate with $M^2$ values greater than 100.

The Applicants have recognized that high power lasers typically have an $M^2>144$. The larger number of modes makes $M^2$ larger and makes it difficult to focus the light into small, low numerical aperture fibers and reduces the ability to project high power density light onto tissue. As a result, the vaporization efficiency of CW arclamp pumped 532 nm lasers on prostate tissue is significantly reduced.

Other aspects and advantages of the present invention can be seen on review of the drawings, the detailed description and the claims, which follow.

SUMMARY OF THE INVENTION

Photoselective vaporization of tissue, such as the prostate for treatment of BPH, is based upon applying a high intensity radiation to prostate tissue using a radiation that is highly absorptive in the tissue, while being absorbed only to a negligible degree by water or other irrigant during the operation, at power densities such that the majority of the energy is converted to vaporization of the tissue without significant residual coagulation of adjacent tissue. Unlike prior art techniques for treatment of BPH, the procedure may be conducted under local anesthesia, and patients are usually able to go home a couple of hours after the procedure. The procedure results in fewer side effects than prior art techniques, including lower incidence of dysuria and hemouria. Patients may be treated without requiring post-operative catherization of the urethra.

According to one embodiment of the invention, a method for treating BPH comprises the steps of providing a solid-state laser having a laser element positioned to receive pump radiation from an excitation source; in some cases modulating the source to cause the laser to emit pulsed laser light; and delivering the laser light to targeted tissue. Various solid-state lasers may be used for this purpose, including (without limitation), a Q-switched laser using a frequency doubling crystal such as potassium-titanyl-phosphate (KTP), pumped using a diode array, an arc lamp or a flash lamp. While Q-switching induces short, "micro-pulses," a "macro-pulse" duration of the laser light is preferably in the range of 0.1 to 500 milliseconds, induced by for example modulating the pump energy with the desired macro-pulse length. The wavelength of the laser light is preferably between 200 and 1000 nm. The laser light is preferably delivered to the targeted prostate tissue through an optical fiber terminating at or near a distal end in a side-firing probe. However the side-firing probe is not essential.

Operation of the solid-state laser in a "macro-pulsed" mode is more efficient in inducing rapid tissue ablation than a CW laser of the same average power. This is in part because the macro-pulsing is more efficient in inducing "char" formation, a mild carbonization in which the tissue typically darkens slightly but does not necessarily turn completely black. Although char formation is not essential to efficient rapid ablation it is helpful because the darkened tissue is better at absorbing light. The macro-pulsed laser is also more efficient and has higher beam quality, with $M^2$ values typically less than 144, than a continuous wave laser with same average output power.

According to a second embodiment of the invention, a method for treating soft tissue comprises the steps of providing a solid-state laser having a laser element positioned to receive pump radiation from a pump radiation source; modulating the pump radiation source to cause the laser element to emit laser light having a pulse duration of between 0.1 milliseconds and 500 milliseconds and an output power exceeding 20 watts; and delivering the laser light to targeted tissue.

According to a third embodiment of the invention, a method for treating BPH comprises the steps of providing a solid-state laser having a laser element positioned to receive pump radiation from a pump radiation source; Q-switching the laser to generate a quasi-continuous wave (CW) beam having an output power exceeding 60 watts; and, delivering the beam to targeted prostate tissue.

According to a fourth embodiment of the invention, a method for treating BPH comprises the steps of providing a solid-state laser having a laser element positioned to receive pump radiation from a pump radiation source such as a laser diode; Q-switching the laser to generate a quasi-continuous wave (CW) beam having an output power exceeding 20 watts with an $M^2$ less than 144; and delivering the beam to prostate tissue.

It has been recognized that as more and more laser energy is consumed by vaporization of the tissue, the amount of laser energy leading to residual tissue coagulation gets smaller, i.e. the amount of residual coagulation drops, and the side effects attendant to the residual injury caused by the surgery drop dramatically. Thus, the extent of the zone of thermal damage characterized by tissue coagulation left after the procedure gets smaller with increasing volumetric power density, while the rate of vaporization increases. Substantial and surprising improvement in results is achieved. It has been recognized that increasing the volumetric power density absorbed in the tissue to be ablated, has the result of decreasing the extent of residual injury of the surrounding tissue. This recognition leads to the use of higher power laser systems, with greater levels of irradiance at the treatment area on the tissue, while achieving the lower levels of adverse side effects and a quicker operation times.

Although the invention can be generalized other types of tissue, one embodiment of the invention provides a method for photoselective vaporization of prostate tissue. According to this embodiment, the method includes delivering laser radiation to the treatment area on the tissue, via an optical fiber for example, wherein the laser radiation has a wavelength and irradiance in the treatment area on the surface of the tissue sufficient because vaporization of a substantially greater volume of tissue than a volume of residual coagulated tissue caused by the laser radiation. In one embodiment, the laser radiation is generated using a neodymium doped solid-state laser, including optics producing a second or higher harmonic output with greater than 60 watts average output power, and for example 80 watts average output power, or more. The laser radiation is coupled into an optical fiber adapted to direct laser radiation from the fiber to the treatment area on the surface of the tissue. For the treatment of prostate, the fiber optic is inserted via transurethral cystoscope, including lumens for delivering irrigants to the treatment area, and for direct visualization during the treatment.

In other embodiments, the delivered laser radiation has a wavelength in a range of about 200 nm to about 650 nm, and has an average irradiance in the treatment area greater than about 10 kilowatts/cm$^2$, in a spot size of at least 0.05 mm$^2$. More preferably, the irradiance is greater than about 20 kilowatts/cm$^2$, and even more preferably greater than about 30 kilowatts/cm$^2$. The spot size in preferred systems is for example less than about 0.8 mm$^2$.

Accordingly, in one embodiment, the second harmonic output of the neodymium dope solid-state laser is applied using a side firing tip on the optical fiber. The side firing tip, which causes a diverging beam to be directed out of the optical fiber, is placed close to the tissue, within about 1 mm from the side of the side firing tip to contacting the side of the tip. Close placement increases the irradiance delivered to the treatment area so that higher irradiance is available with solid-state lasers generating a 60 to 80 watts average output power.

According to the present invention, the efficiency of the vaporization and the reduction of injury to residual tissue are sufficient that the procedure may be carried out while applying only local anesthetic during the delivery of laser energy, and throughout the procedure. For example, a procedure according to the present invention includes applying intraurethral topical anesthesia such as lidocaine, either a periprostatic block or a perirectal block, oral and/or intravenous drugs such as Fentanyl or Demerol, chilled irrigant, and irrigant containing anesthesia.

Furthermore, embodiments of the invention include the delivery of the laser energy using a Q-switched, solid-state laser which produces micro-pulses in combination with applying pump power to the laser medium in a sequence a pulses so that output radiation is produced in macro-pulses having a peak power of greater than 200 watts, and more preferably about 240 watts or greater. The peak irradiance in the treatment area during the pulses is thereby substantially increased, and preferably greater than 50 kilowatts/cm$^2$, and as much as 90 kilowatts/cm$^2$ in some embodiments of the invention.

Other aspects and advantages of the present invention can be seen on review the figures, the detailed description, and the claims which follow.

BRIEF DESCRIPTION OF THE DRAWINGS

FIG. 8 illustrates absorption depth in prostate tissue for 532 nm light.

FIG. 9 illustrates absorption depth in prostate tissue for 1064 nm light.

FIG. 10 is a diagram of a beam path from an end view of a side firing tip, according to one embodiment of the present invention.

FIG. 11 is a diagram of a beam path from a side view of the side firing tip of FIG. 10, according to one embodiment of the present invention.

DETAILED DESCRIPTION

Figure 1:
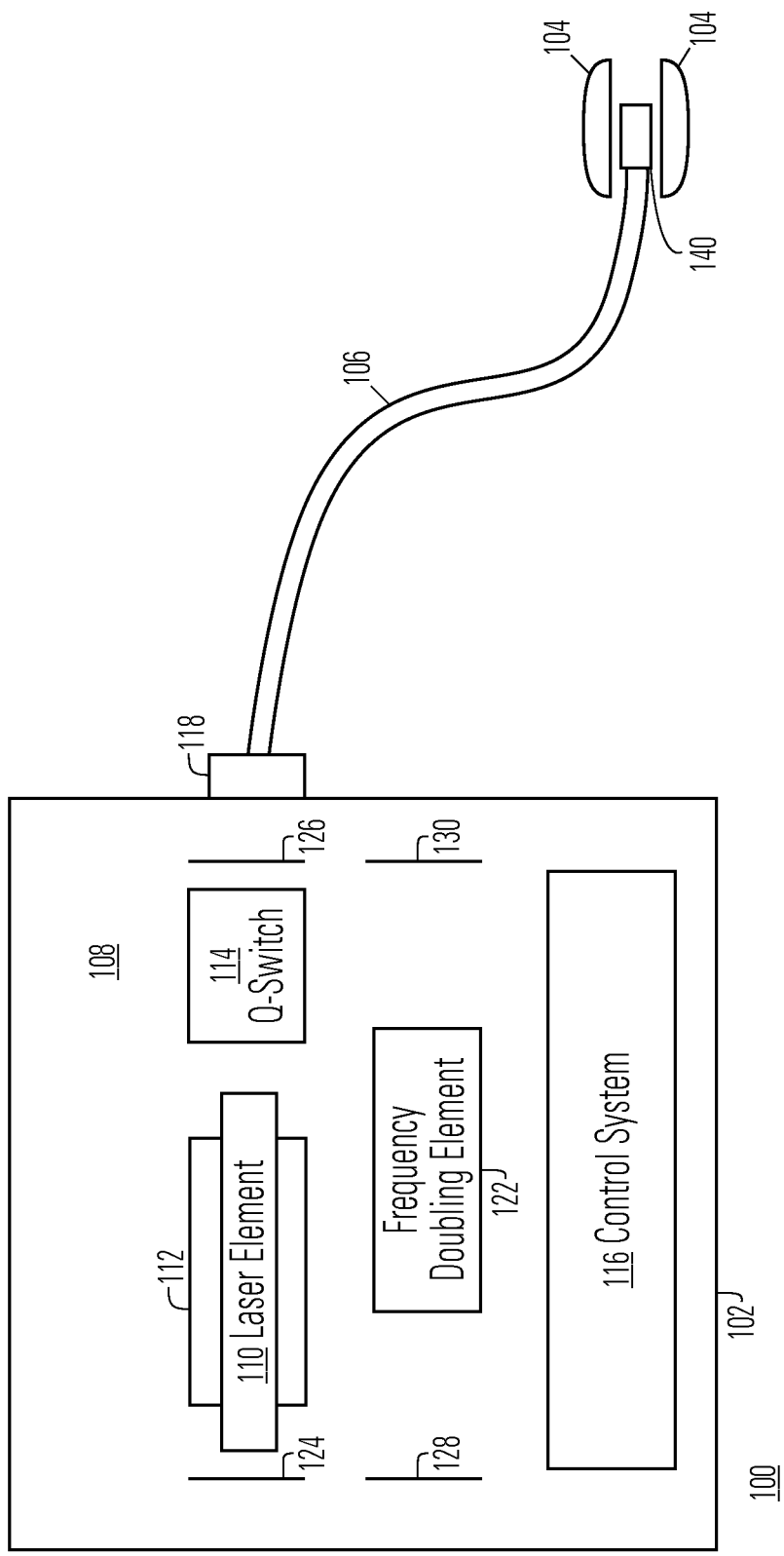
FIG. 1 depicts a laser system for implementing the tissue ablation methods of the invention.

FIG. 1 is a block diagram depicting an exemplary laser system 100 which may be employed for implementing the present invention. Laser system 100 includes a solid-state laser 102, which is used to generate laser light for delivery through optical fiber 106 to target tissue 104. As will be discussed in further detail herein below, laser 102 is capable of being operated in a "macro-pulsed" mode, wherein the laser light is emitted as macro-pulses having relatively long pulse durations.

Laser 102 more specifically comprises a laser element assembly 110, pump source 112, and frequency doubling crystal 122. In the preferred embodiment, laser element 110 outputs 1064 nm light which is focused into frequency doubling crystal 122 to create 532 nm light. According to one implementation, laser element assembly 110 may be neodymium doped YAG (Nd:YAG) crystal, which emits light having a wavelength of 1064 nm (infrared light) when excited by pump source 112. Laser element 110 may alternatively be fabricated from any suitable material wherein transition and lanthanide metal ions are disposed within a crystalline host (such as YAG, Lithium Yttrium Fluoride, Sapphire, Alexandrite, Spinel, Yttrium Orthoaluminate, Potassium Gadolinium Tungstate, Yttrium Orthovandate, or Lanthanum Scandium Borate). Laser element 110 is positioned proximal to pump source 112 and may be arranged in parallel relation therewith, although other geometries and configurations may be employed.

Pump source 112 may be any device or apparatus operable to excite laser element assembly 110. Non-limiting examples of devices which may be used as pump source 112, include: arc lamps, flashlamps, and laser diodes.

A Q-switch 114 disposed within laser 102 may be operated in a repetitive mode to cause a train of micro-pulses to be generated by laser 102. Typically the micro-pulses are less than 1 microsecond in duration separated by about 40 microseconds, creating a quasi-continuous wave train. Q-switch 114 is preferably of the acousto-optic type, but may alternatively comprise a mechanical device such as a rotating prism or aperture, an electro-optical device, or a saturable absorber.

Laser 102 is provided with a control system 116 for controlling and operating laser 102. Control system 116 will typically include a control processor which receives input from user controls (including but not limited to a beam on/off control, a beam power control, and a pulse duration control) and processes the input to accordingly generate output signals for adjusting characteristics of the output beam to match the user inputted values or conditions. With respect to pulse duration adjustment, control system 116 applies an output signal to a power supply (not shown) driving pump source 112 which modulates the energy supplied thereto, in turn controlling the pulse duration of the output beam.

Although FIG. 1 shows an internal frequency doubled laser, it is only by way of example. The infrared light can be internally or externally frequency doubled using non-linear crystals such as KTP, Lithium Triborate (LBO), or Beta Barium Borate (BBO) to produce second harmonic 532 nm green light, and higher harmonics. The frequency doubled, 532 nm wavelength and the shorter wavelength higher harmonic beams are better absorbed by the tissue, and promote more efficient tissue ablation.

In one preferred embodiment the resonant cavity control system is that described in U.S. Pat. No. 5,151,909, which is incorporated by reference as if fully set forth herein.

Laser 102 further includes an output port couplable to optical fiber 106. Output port 118 directs the light generated by laser 102 into optical fiber 106 for delivery to tissue 104. Mirrors 124, 126, 128, and 130 direct light from the lasing element 110 to the frequency doubling crystal 122, in addition to forming the resonant cavity of the laser. Mirrors 124, 126, 128, and 130 are configured for focusing the light to form an image just in front of the frequency doubling crystal 122 on the side closer to mirror 130, and to compensate for thermal lensing in the lasing element. Although mirrors 124, 126, 128, and 130 are illustrated as flat and parallel to the walls of the laser, typically the focusing is achieved by curving and/or angling the mirrors. Alternatively transmissive optical elements could be used to focus the light and compensate for the thermal imaging. Mirrors 124, 128 and 130 reflect both the wavelength of light produced by the lasing element (e.g. 1064 nm) and the wavelength of the frequency doubled light (e.g. 532 nm). Mirror 126 only reflects the light originating from the lasing element 110 (e.g. 1064 nm) but is transparent to the frequency doubled light (e.g. 532 nm), forming an output window. Higher harmonic outputs may also be generated from the 1064 nm line, or other line amplified in the laser, including third and fourth harmonics, for shorter wavelengths. Other laser systems may be used, including but not limited to Sapphire lasers, diode lasers, and dye lasers, which are adapted to provide the output power and wavelengths described herein, including wavelengths in the ranges from 200 nm to 1000 nm and from 1100 nm to 1800 nm, for example.

While a bare fiber may be utilized for certain procedures, optical fiber 106 preferably terminates in a tip 140 having optical elements for shaping and/or orienting the beam emitted by optical fiber 106 so as to optimize the tissue ablation process.

Figure 2:
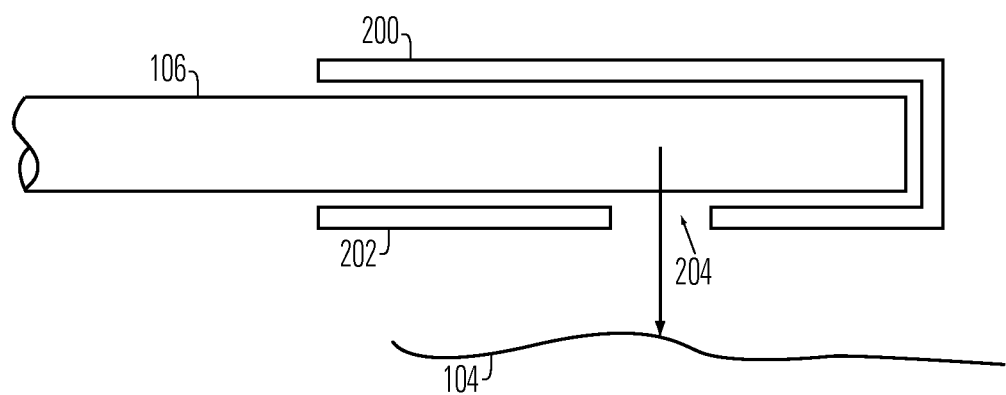
FIG. 2 depicts a side-firing probe for use with the system of FIG. 1.

FIG. 2 depicts a side-firing probe tip 200, which may be used as tip 140 (FIG. 1). The tip 140 is treated to deflect light sideways. Some examples of methods for deflecting the light sideways are to include a light scattering material in the tip 140 and/or to place a reflective element in the tip 140. The reflective element could be angled at 45°, for example; to deflect the light at 90° with respect to the axis of the fiber 106. Side-firing probe tip 200 includes an optically transparent sleeve 202 having a transparent window 204 (which may be constructed as a cutout in the wall of sleeve 202 through which the beam is emitted in a direction transverse to the optical axis of fiber 106.) An acceptable range of angles in which to deflect the light beam is between about 40 to 120 degrees with respect to the axis of the fiber. The preferred embodiments use an angle of either 70 or 100. The angle of 80° is preferred from the standpoint of the ease in manufacturing the tip 200 and the angle of 90° is preferred from the standpoint of the ease in aiming the side firing light.

In a typical mode of operation, optical fiber 106 is held within an endoscope such as a cystoscope or similar instrument that allows the clinician to precisely position the distal end of the optical fiber adjacent to the targeted tissue. The endoscope also has channels for supplying and removing an irrigant solution to and from the tissue. In addition, light and image guides are also included for illuminating and imaging the tissue so that the clinician may direct the laser light and assess the progress and efficacy of the ablation procedure.

Figure 3:
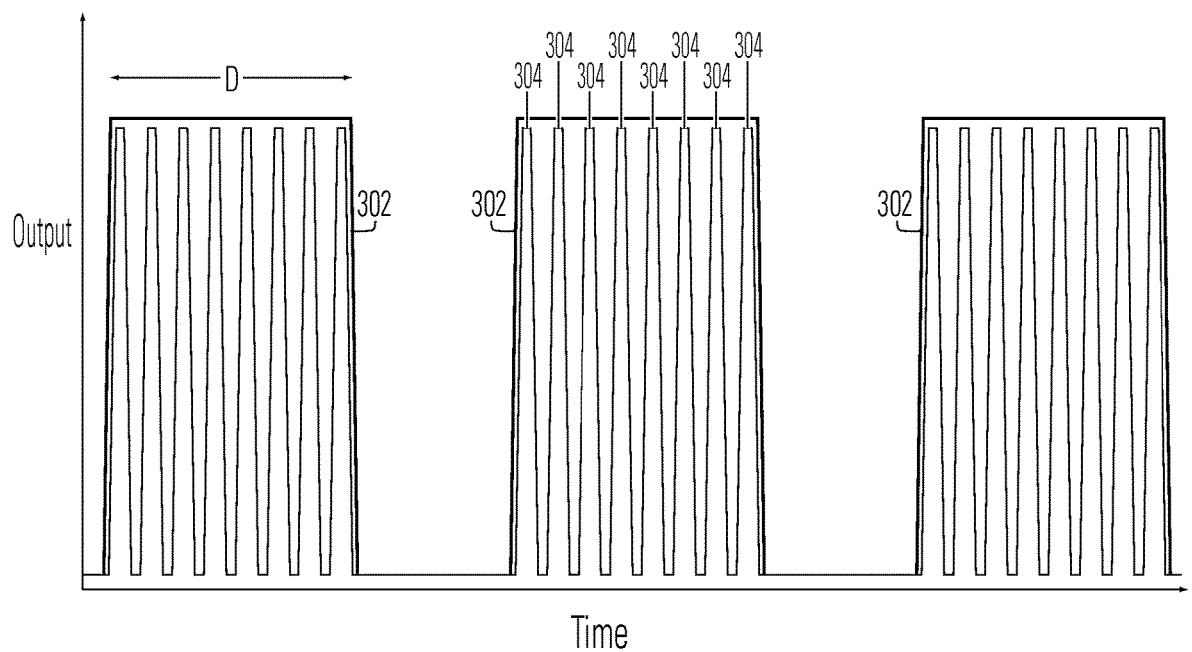
FIG. 3 depicts an exemplary output waveform of the FIG. 1 laser when the laser is operated in a macro-pulsed mode.

FIG. 3 illustrates an exemplary output waveform applied to tissue 104 when laser 102 is operated in the macro-pulsed mode. Each macro-pulse 302 is defined by a train of Q-switched micro-pulses 304. While a relatively small number of micro-pulses 302 are depicted for purposes of clarity, an actual macro-pulse may comprise hundreds or thousands of component micro-pulses 304. In the preferred embodiment there are between 2 and 12,200 micro-pulses per macro-pulse.

An arc lamp, for example, when used as the pump source 112, is kept at a low power level between pulses that are preferably just enough to maintain the arc. These low pump powers are below the lasing threshold of the laser; as a consequence, there is no laser output between macro-pulses.

As mentioned above, the pulse duration or width D (FIG. 3) of the output beam is governed by the modulation of pump source 112, and more specifically by the period during which the pump source 112 is maintained in an "on" or high-power condition. In other words, the longer the pump source 112 is maintained in an on condition, the longer the pulse width. Typically, laser 102 will be capable of delivering pulses 302 having pulse durations D in the range of 1 to 20 milliseconds (2 to 490 micro-pulses) or 1 to 50 milliseconds (2 to 1,220 micro-pulses) and average output powers preferably exceeding 60 watts and preferably up to 100 or 200 watts. The ratio of D to the period of the macro-pulses defines the duty cycle, which is typically between 10 and 50%.

In accordance with one embodiment of the invention, a laser system 100 of the foregoing description is employed to treat BPH by ablating targeted prostate tissue 104. The clinician may utilize an endoscope or similar instrument to guide the distal end and tip 140 of optical fiber 106 into alignment with the targeted prostate tissue 104. Laser system 100 is then operated in the macro-pulsed mode so that laser 102 generates laser light having the pulsed waveform depicted in FIG. 3 and delivers it through optical fiber 106 to tissue 104.

It is known that irradiation of prostate tissue 104 may initially cause tissue heating resulting in the formation of a char layer. This char layer is highly optically absorptive in the wavelengths emitted by laser 102, which thereby facilitates efficient absorption of the laser light and resultant ablation of tissue 104. However, the formation of the char layer is not essential for efficient ablation. Prior art techniques for treatment of BPH by laser ablation (such as the technique described by Kuntzman et al. in "High-Power (60-Watt) Potassium-Titanyl-Phosphate Laser Vaporization Prostatectomy in Living Canines and in Human and Canine Cadavers," Urology, Vol. 49, No. 5 (1997)) utilized a quasi-CW laser to irradiate the prostate. Although such lasers do produce moderately high average powers, they have a large number of transverse modes and as such, produce highly divergent light when focused into small fiberoptics. This leads to less than optimal power densities when the laser light is directed at tissue. As a consequence, these lasers are not particularly efficient at inducing formation of a char layer, and ablation rates are relatively slow, significantly lengthening procedure times. Further, since formation of the char layer takes place at relatively low rates, undesirable thermal damage to deeper tissue layers may occur. In contrast, it has been found that a macro-pulsed beam, such as that generated by laser 102, promotes rapid formation of a char layer even at moderate output energy levels, thereby helping to accelerate ablation rates and reducing procedure time.

The macropulsing can also increase efficiency because the threshold voltage required for lasing while macropulsing (the operating threshold) is lower than the initial threshold voltage for lasing (cold threshold).

Macropulsing is also more efficient for producing green light because the conversion of infrared light to frequency doubled light increases as the square of the infrared light intensity. The higher peak powers of the macro-pulsed infrared light leads to higher second harmonic conversion efficiency. For example, at any given time, the input power and output power of a frequency-doubled laser using KTP are related according to $$Po = A(Pi)^2,$$

Where A is an experimentally determined positive constant. This equation relates the peak input power to the peak output power. However, the average input power and output power for a duty cycle of k percent are given by $$<Pi> = k(Pi) \text{ and}$$

$$<Po> = k(Po) = kA(Pi)^2 = A(<Pi>)^2/k,$$

where the brackets "< >" indicate an average value of the enclosed quantity. Thus, decreasing the duty cycle from 100% to 50% (i.e. reducing k from 1 to 0.5) while simultaneously doubling the peak input power Pi results in no change to the average input power <Pi> and a doubling of the average output power <Po>. Pulse modulating or macropulsing using Q-switching, for example, enables reaching higher average output powers with less thermal lensing due to the lower input power.

Additionally, it is possible that the frequency doubling crystal has nonlinearly increasing output power as a function of the input power. In other words the second derivative of the output power with respect to the input power may be positive, in which case the rate of increase of the output power increases with increasing input power. Specifically, in such a case the functional dependence of the instantaneous or peak output power, Po, on the instantaneous or peak input power, Pi, is such that $$d^2(Po)/d(Pi)^2 > 0.$$

When this is true, and Po is an increasing function of Pi, the higher peak input power results in a more efficient laser because ratio of the output to input power increases.

Pump source modulation of the laser can produce high peak power macro-pulses and affect the efficiency of the average power output. Macro-pulse in excess of a steady state power can substantially improve the initiation of the vaporization of prostate tissue. The higher peak power of the macro-pulse rapidly initiates charring which in turn serves as an additional chromophore for the incident energy and enhances the vaporization rate. A 30% macro-pulse duty cycle is sufficient to increase the average power output of an arc lamp pumped laser to greater than 80 watts. Additionally the pump modulation generates macro-pulse with pulse powers greater than 240 watts.

By way of a non-limiting example, prostate tissue 104 may be efficiently and rapidly ablated when laser 102 is operated at an output power of 80 to 100 watts, a pulse duration of 1-50 milliseconds, and a wavelength of 532 nm.

In accordance with a second method embodiment of the invention, laser system 100 may be utilized to ablate other types of tissue 104. Treatment of tissue 104 is performed in a manner substantially identical to the technique for treating BPH disclosed above. The clinician may utilize an endoscope or similar instrument to guide the distal end and tip 140 of optical fiber 106 into alignment with the prostate tissue 104. Laser system 100 is then operated in the macro-pulsed mode so that laser light having the pulsed waveform depicted in FIG. 3 is generated by laser 102 and delivered through optical fiber 106 to tissue 104. To achieve adequate results, laser system 100 is adjusted to emit a beam having a pulse duration between 0.1 and 500 milliseconds, and an output power of at least 20 watts. Upon vaporization of the required volume of tissue 104, (which may be assessed via an imaging channel contained in the endoscope), the output beam of laser 102 is turned off.

Figure 4:
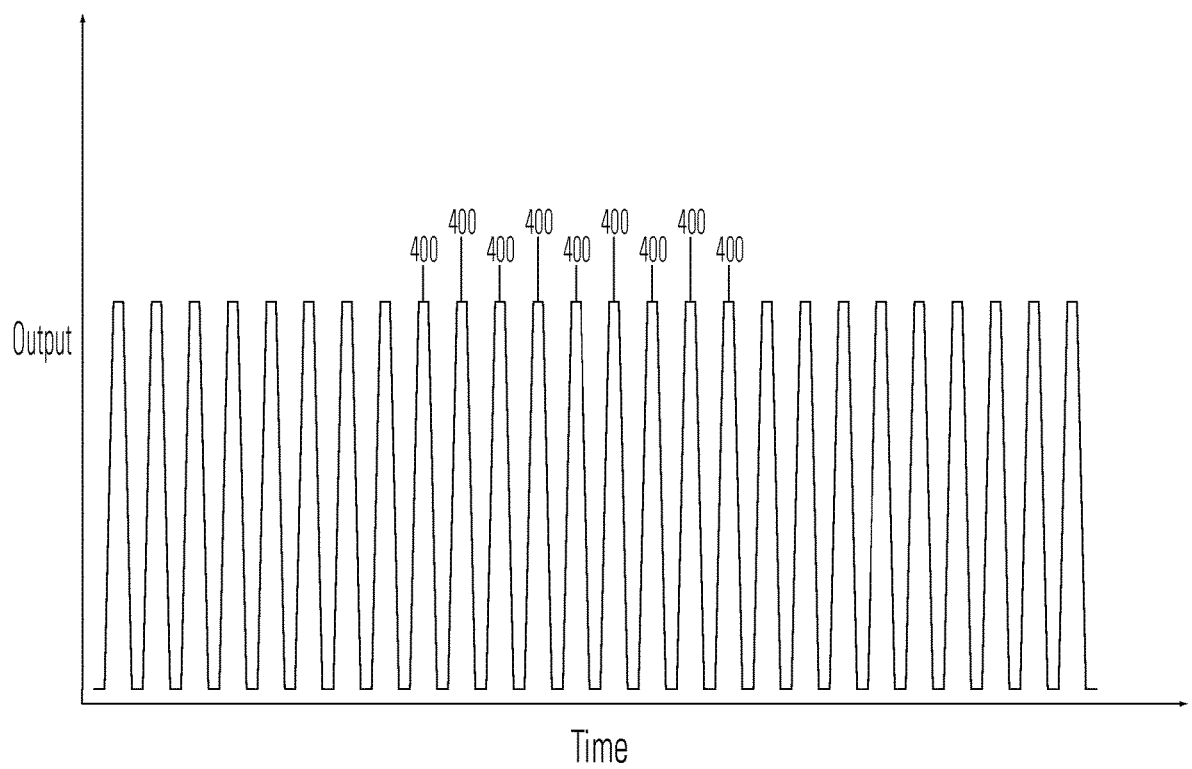
FIG. 4 depicts an exemplary output waveform of the FIG. 1 laser when the laser is operated in a quasi-CW mode.

In a third method embodiment of the invention, treatment of BPH is effected by operating laser 102 in a quasi-CW mode at an output power greater than 60 watts. The increased denaturization of the tissue is dramatic with increases in power, suggesting a threshold effect. As depicted in FIG. 4, laser 102 generates a continuous train of Q-switched micro-pulses 400 when operated in quasi-CW mode. The laser light is then delivered via optical fiber 106 to targeted tissue 104. Operation in a quasi-CW mode at powers above 60 watts facilitates formation of char and consequent rapid ablation rates, whereas operation in a quasi-CW mode at powers below 60 watts forms char more slowly and causes more thermal damage to underling tissue.

A fourth embodiment of this invention is to produce a high power, high beam quality laser that can project high power density laser light onto tissue. To do this the number of transverse optical modes supported by the resonator needs to be kept as low as possible.

Small $M^2$ and high average powers can be achieved by reducing the degree of thermal lensing in the laser element. Using laser diodes as the excitation source is one effective way of greatly reducing both the size of the lasing element and the thermal gradient responsible for creating the thermal lens. The reason for this is that while 2-10% of the light produced from a flashlamp or arc lamp is converted into useful laser light 30-60% of the light emitted from laser diodes can be converted to laser light. Since the energy that is not converted to laser light is converted into heat, laser diodes deposit significantly less heat in the lasing element and as a consequence create a less powerful thermal lens. In this manner laser diodes can be used to pump crystalline laser elements or fiber lasers to produce high beam quality lasers. Slab and waveguide lasers that can be pumped by laser diodes, arc lamps, or flashlamps are another method of creating low $M^2$ lasers. This is because the thermal gradient produced in slab lasers is linear across the thin dimension of the slab and not radially dependent in contrast to a typical cylindrical lasing element. The linear thermal gradient does not produce a thermal lens resulting in low $M^2$ values.

For example, as a result of the low $M^2$ some embodiments of this invention are capable producing laser light that upon exiting a flat end of a fiber having a diameter of 600 µm has a divergence of 15.3° or lower; 15° or lower; 10° or lower; or 5° or lower, and the power density can be 13,400 watts per $cm^2$, or greater.

Figure 5:
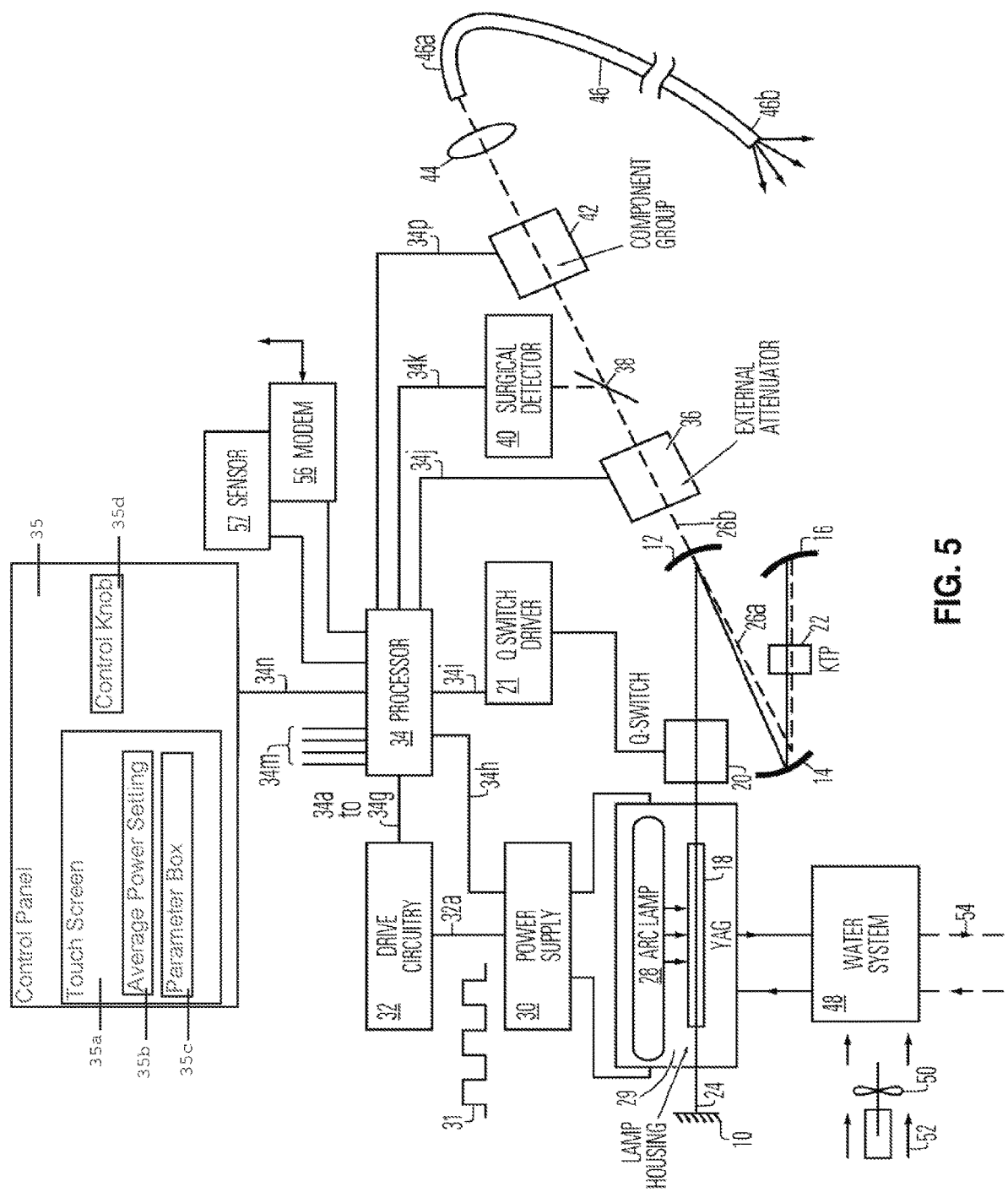
FIG. 5 is a block diagram of a laser system adaptable for use according to the present invention.

FIG. 5 shows a block diagram of a preferred laser system according to the present invention. In FIG. 5, a laser resonator is defined by end mirror 10, turning mirrors 12 and 14, and end mirror 16. All of these mirrors are high reflecting (greater than 99.8%) at the 1064 nm line. An optical path 24 is defined by these mirrors. A gain medium 18 comprising a Nd:YAG rod is mounted along the optical path within a lamp housing 29. An arc lamp 28 is also mounted within the housing and supplies pump power to the gain medium in response to current generated in power supply 30. Also in the optical path 24 is a Q-switch 20 between the lamp housing 29 and the turning mirror 12. A non-linear crystal 22 is mounted between the turning mirror 14 and the back mirror 16. This non-linear crystal is preferably a KTP crystal aligned for frequency doubling to generate a 532 nm beam. Mirrors 16 and 14 are highly reflective at 532 nm, while mirror 12 is transmissive and operates as an output coupler for the 532 nm beam.

Thus, the laser resonator is designed for resonating at a first frequency, i.e., 1064 nm along the Z-shaped optical path 24. A second frequency derived from the 1064 nm beam is generated in the KTP crystal 22. This beam travels along the path 26a and is extracted from the resonator to supply an output beam along path 26b.

The output beam along path 26b passes through a controllable attenuator 36, a beam splitter 38, which supplies a portion of the output beam to a surgical detector 40, and a component group 42 as described in more detail below. The attenuator, detector, and component group are all coupled to a data processing system 34, across lines 34j, 34k, and 34p.

The Q-switch 20 is controlled by Q-switch driver 21, which is, in turn, coupled to data processor 34 across line 34i. In the preferred system, the Q-switch is an acoustic-optic Q-switch.

Similarly, the power supply 30 generates an electrical power signal for controlling the arc lamp 28. This power signal is controlled by the data processor 34 across line 34h and by drive circuitry 32 across line 32a. Drive circuitry 32a is controlled by the data processor across lines 34a through 34g. A sensor 57 is coupled with the data processor to sense an environmental condition, such as temperature or humidity, that affects operation of the laser system. A modem 56 is connected to the data processor 34, providing an interface for remote access to memory in the data processor. Finally, a control panel 35, by which a user can supply input signals and parameters, is provided. This control panel 35 is connected to the data processor 34 across line 34n.

In alternative systems, the non-linear crystal may be mounted outside the resonant cavity of the resonator. Also, it may be used for extracting outputs other than the second harmonic, such as sum-of-frequency derivation or the like.

The wavelength used according to the present invention for BPH treatment should be strongly absorbed in the prostate tissue to help initiate and maintain tissue vaporization without creating deep tissue heating. The wavelength also must be minimally absorbed by the irrigant it used during the procedure, typically water. The 532 nm light produced by the system of FIG. 5, is both strongly absorbed in oxyhemoglobin and weakly absorbed in water. Oxyhemoglobin is readily present in prostate tissue and serves as an efficient chromophore for 532 nm light. The differential in absorption coefficients between oxyhemoglobin and water at 532 nm is approximately 5 orders of magnitude ($10^5$). In other embodiments, wavelengths in the range from 200 nm-650 nm are used, which have strong oxyhemoglobin absorption and relatively weak water absorption ($>10^2 \times$). In yet other embodiments, wavelengths in the range from 200 nm to 650 nm range are used, which have strong oxyhemoglobin absorption and relatively weak water absorption ($>10 \times$).

Figure 6:
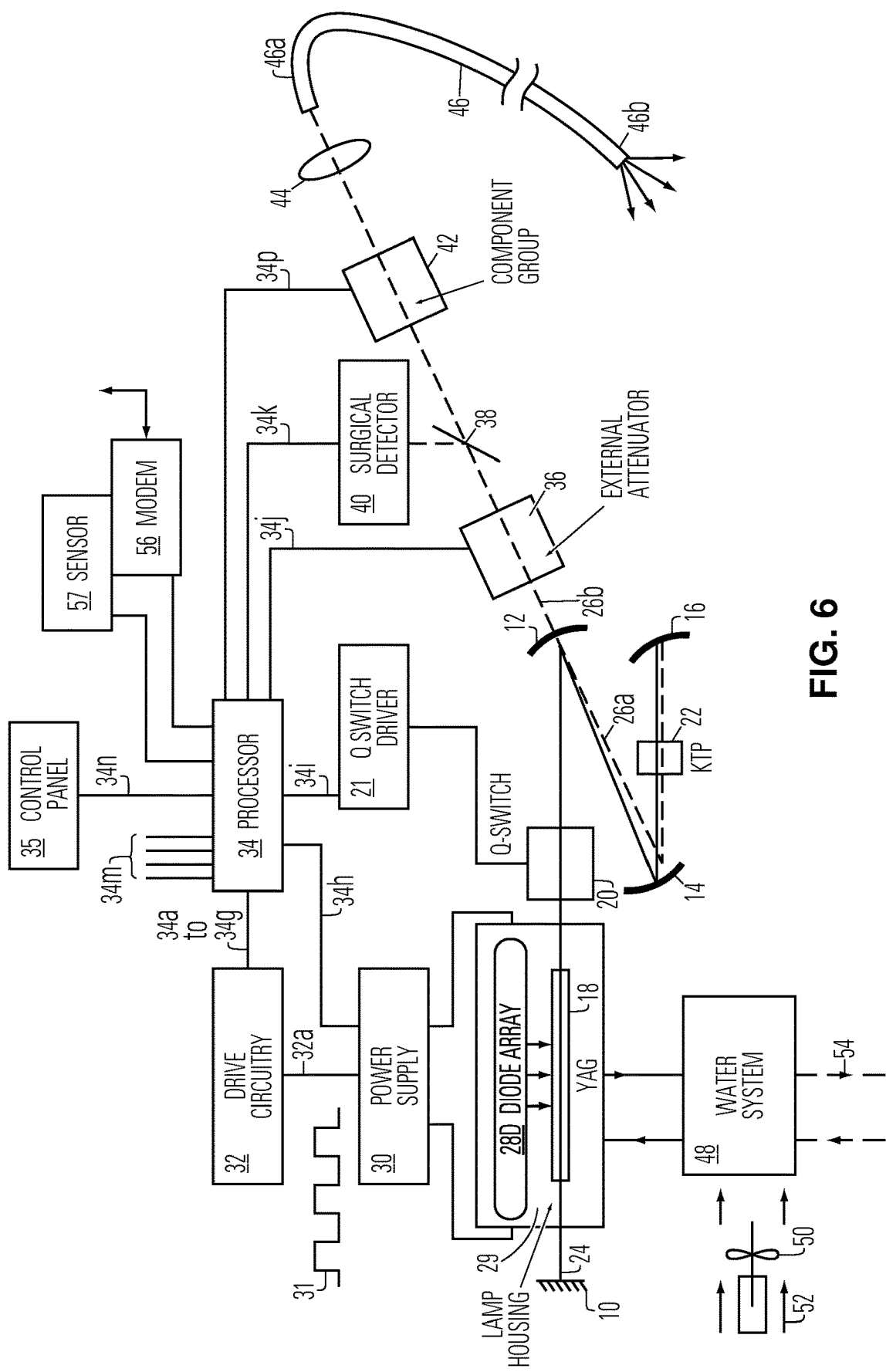
FIG. 6 is a block diagram of an alternative laser system adaptable for use according to the present invention.

Of course, as shown in FIG. 6, in which like components have the same reference numerals as in FIG. 5, alternative pump power sources, such as laser diode arrays, other lasers for longitudinal pumping, and others, can be used as suits the needs of a particular gain medium and application of the laser system. Representative laser diodes include laser diodes providing output in the range of 805 to 820 nm in wavelength with an input power to the array of pumping diodes in the range of 300 to 500 Watts. The laser diodes used for pump energy are operated in a modulated macro-pulse mode, or in a continuous mode, as suits a particular implementation.

The laser systems shown in FIGS. 5 and 6 can be modified by removing both the Q-switch and the external surgical attenuator. The Q-switch and surgical attenuator are removed because the modulated pump power provides a great deal of flexibility in controlling the output power of the laser not attainable using a Q-switch. The data processing system can be programmed to maintain a constant thermal load in the laser system while varying the peak pump power widely. Thus, the peak current and duty cycle of the pump power source can be adjusted in such a way to keep the average pump power constant, but the second harmonic power during the ready and work modes adjusted by selecting the peak current and duty cycle. Although it may be necessary to use attenuators in the beamline during the ready mode in order to extract an aim beam, such attenuators may well be eliminated for the work mode. The average power does not have to be constant, rather it can be maintained at levels which keep thermal focusing of the gain medium within the range of stability of the resonator.

A representative laser system adapted for delivery of energy as described above, comprises an 80 watt average power, 532 nm output wavelength, solid state, intra-cavity frequency doubled Nd:YAG laser. To obtain optimal efficiency, an arc lamp pump source is modulated at a period of 4.5 ms with a 16 ms duty cycle, generating 285 watts peak macro-pulse power. An intra-cavity acousto-optic AO Q-switch is used to further modulate the energy at a period of 40 kHz with a 450 us micro-pulse. The laser energy is coupled to a side firing fiber optic delivery device for delivery to prostate tissue.

The laser system uses a combination touch screen 35a (referring to FIG. 5) and control knob user interface 35d to assist the operator in setting up the surgical parameters, including power levels and pulse sequence specifications. The average power setting 35b is prominently displayed on the screen. Parameter adjustments are made by first activating (touching) the desired parameter box 35c on the screen and then turning the knob. The laser system uses a secure card key interface to enable the laser. The system is transportable. The system offers convenient storage and a fiber delivery device pole.

Figure 7:
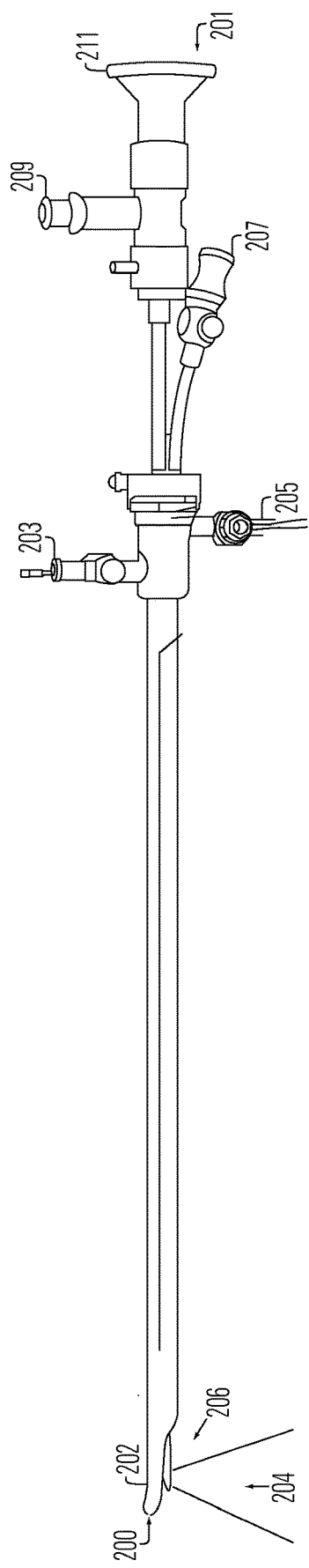
FIG. 7 is a diagram of a transurethral cystoscope, adaptable for use according to the present invention.

An example of an endoscope, in particular a transurethral cystoscope, for use with the present invention is shown in FIG. 7. The cystoscope has a distal end 200 and a proximal end 201. The distal end 200 includes a tongue member 202 for pushing tissue away from a treatment area in the region 204. Laser radiation is directed sideways from opening 206 in to the region 204, by a side firing fiber optic component. Water or saline solution is delivered and removed from the treatment area via lumens in the probe. A viewing optic is also placed in the opening 206, by which the surgeon is able to view the treatment area during the procedure. On the proximal end 201 of the cystoscope, an input port 203 and an output port 205 for flow of the irrigant is provided. Also, a fiber port 207 is used for insertion and removal of the fiber optic delivering laser radiation to the treatment area. A light source connector 209 is used for supplying light to the treatment area for visualization. A telescope 211, which can be coupled to a video camera, or looked into directly, is also included on the representative cystoscope.

The vaporization of prostate tissue using oxyhemoglobin as the primary chromophore is related to the incident power density, or irradiance, which can be expressed in Watts/cm$^2$. The overall rate of prostate tissue vaporization is a function of the spot size, absorption depth, and the power density. A large spot with high power density, and rapid absorption is ideal to rapidly vaporize tissue. A high power light source is required to achieve a large spot, high power density treatment beam. Peak laser power, average laser power, beam quality, delivery device design and delivery device placement all affect the efficiency of vaporization. A treatment beam 28.5 Kw/cm$^2$ average irradiance with a 85.5 Kw/cm$^2$ peak irradiance macro-pulse, with a spot size between about 0.2 and 0.5 mm$^2$, rapidly vaporizes tissue.

The BPH treatment procedure can be outlined as follows for one embodiment of the invention, using a laser system as described above with reference to FIG. 5.

Equipment/Set-up
21-24 french continuous flow cystoscope
Laser
Side firing probe
Filter (eye safety filter for the monocular or the video camera)
Sterile water
Cystoscope eye piece or video system for direct visualization
Anesthesia
Any of the following or combinations of the following:
General, spinal nerve block, topical, periprostatic block, perirectal block, pudental block & intervenous drugs
This procedure does not require general or spinal anesthesia
Technique/Process
Prep patient following standard protocol for cystoscopic procedures
Administer anesthesia
Dilate the urethra
Insert cystoscope
Insert side firing delivery device
Begin flow of sterile water
Cystoscopy to assess gland
Position fiber near tissue to be removed and active the laser
Use a sweeping motion to vaporize desired tissue
Continue vaporization until the capsule is reached
Monitor vaporization efficiency, remove and clean fiber as required
Debulk desired lobes, median & lateral lobes
Fill bladder with water, remove cystoscope, observe discharge
If necessary insert foley catheter The rapid vaporization with thin coagulation zone contribute to the hemostasis during the procedure. Because of minimal thermal damage to existing tissue, there is a low incidence of side effects, making such symptoms as Dysuria, Incontinence and Impotence which often occur in prior art techniques, very unlikely.

Further, the procedure causes minimal bleeding. Great outcomes are achieved for patients suffering BPH, including improved urine flow rate, improved post-void residual, and improved symptom scores on BPH tests. The procedure often achieves immediate obstruction relief, and post operative catheterization is not always required.

A typical photoselective vaporization of the prostate PVP procedure will use the following steps:

A. At the investigator discretion, van buren sound the urethra in a standard fashion prior to insertion of the continuous flow cystoscope.

B. Subjects will be administered general, spinal or local (prostatic block & oral and topical anesthesia) anesthesia at the discretion of the Surgeon. In some embodiments, the procedure is performed without the use of general anesthesia or spinal nerve blocks, using only local anesthesia such as any combination of intraurethral topical anesthesia such as lidocaine, either a periprostatic block or a perirectal block, oral and/or intravenous drugs such as Fentanyl or Demerol, chilled irrigant, and irrigant containing anesthesia.

C. Vaporization will be performed with the Laserscope ADD (Angled Delivery Device) fiber, which is a 600 um bare fiber with a quartz capsule over the 70 degree lateral deflecting quartz element and a spot diameter of 1.2 mm at 2 mm.

D. The laser fiber will be introduced through the lumen of a standard 22 Fr continuous flow laser cystoscope, and sterile water will be used as the irrigant.

E. KTP laser energy will be generated by a high power 532 nm laser capable of delivering 80 W of KTP laser power to tissue.

F. Lasing will be performed under direct visualization using a free beam technique, holding the fiber 1-2 mm away from the tissue and vaporizing the lateral lobes beginning at the bladder neck.

G. The visible laser beam will be slowly moved along the length and breadth of the lateral lobe as the tissue is vaporized. The laser will be carefully directed toward the apical tissue making sure to protect the external sphincter.

H. Both lateral lobes will be vaporized evenly to the level of the capsular fibers.

I. The median lobe will be vaporized evenly to the level of the transverse fibers of the vesicle neck. If the median lobe is too large, then it should be partially vaporized before ablation of the lateral lobes to facilitate the movement of the scope and irrigation, and then the remainder will be flattened out later during the procedure.

J. The procedure should preserve the distal crista urethralis and the verumontanum.

K. The end point of the procedure should be judged by the size and appearance of the large transurethral resection-like cavity and by the diminished efficacy of the vaporization effect at the prostatic capsule. The median and lateral hypertrophic tissue must be vaporized to the level-of the transverse fibers and any lingering loose fibers should be removed prior to completion of the treatment.

L. Rarely will arterial bleeders be encountered, however, if an arterial bleeder is encountered, then coagulate the vessel at a distance of approximately 3 to 4 mm.

M. The cystoscope is removed and, if necessary, a foley catheter is inserted at the physician's discretion.

N. This is an outpatient procedure and subjects will be released from the hospital as outpatients per the discretion of the Surgeon.

FIGS. 8 and 9 illustrate the different optical penetration depths of the 532 nm wavelength and 1064 nm wavelength used in prior art procedures. See, S. L. Jacques. *Laser-tissue interaction. Photochemical, photothermal, and photomechanical*. Surg. Clin N. Am. 1992; 72(3):531-558. The optical penetration depth of the 1064 wavelength beam from Nd:YAG laser beam is about 10 mm, which is 13 times larger than the penetration depth of the second harmonic 532 wavelength laser beam, which is about 0.8 mm. As a result, the 1064 laser power is spread out over a much larger tissue volume than the power of the KTP laser. In case of the 1064 laser as shown in FIG. 9, the temperature at the tissue surface barely reaches 100° C. Therefore, only a small portion of tissue gets vaporized. But a huge volume of tissue gets coagulated (see space between 100° C. and 60° C. isotherm). The consequences are the formation of edema in a huge volume of coagulated tissue, swelling of the prostate, and the patient going into retention with catheterization times of several weeks.

The 532 laser beam, in contrast, is substantially completely absorbed within less than about 1 mm of the surface of prostatic tissue. The laser power is confined to a very small tissue volume. The high volumetric power density results in a fast heating of the tissue and efficient tissue vaporization. Volumetric power density delivered to tissue is a function of the absorbtion depth, irradiance in Watts/cm$^2$ and spot size on the surface of the tissue. The coagulation zone is very thin because of the small optical penetration depth of the 532 wavelength, and because substantially all of the radiation is converted to vaporization rather than residual heat.

Other wavelengths which are substantially completely absorbed within less than about 1 mm of the surface of the prostatic tissue include wavelengths less than about 650 nm, for example between about 200 nm and 650 nm.

FIGS. 10 and 11 illustrate a profile of a beam delivered to tissue using one representative side firing optical fiber, to show spot size as a function of distance from the side of the optical fiber. FIG. 10 is an end view, showing a fiber 600, cladding 601 on the fiber, an air space 602, and a tip 603 through which the beam is directed by a reflecting face on the fiber. The cross-section of the beam is represented by the crossing lines 604 and 605. As shown, the beam has a width in this dimension of about 0.35 mm at 1 mm from the side of the tip 603. At about 2 mm from the side of the tip 603, the width is about 1 mm. At about 3 mm distance from the side of the tip 603, the beam width is about 2.2 mm.

FIG. 11 is a side view, with like components given the same reference numbers. The beam width in this dimension is represented by lines 606 and 607. As shown, the beam has a width in this dimension of about 0.7 mm at 1 mm from the side of the tip 603. At about 2 mm from the side of the tip 603, the width is about 1 mm. At about 3 mm distance from the side of the tip 603, the beam width is about 1.5 mm.

Thus, the spot size at 1 mm from the side of the tip is defined basically by an elipse having a major axis of 0.7 mm, and a minor axis of 0.35 mm. The area of the spot at 1 mm is around 0.2 mm$^2$. At 2 mm from the side, the area of the spot is about 0.8 mm$^2$.

For rapid procedures, according to the present invention, the spot size should be large enough that the operator can remove tissue at a reasonable rate, and see the results of a single pass of the spot over a region of tissue. If the spot size is too small, the rate of the operation is too slow. Also, if the spot size is too big, then the procedure is difficult to control precisely. A preferred spot size is less than about 1 mm$^2$, and more particularly between about 0.8 mm$^2$ and about 0.05 mm$^2$. Other apparatus may be used for delivery of the beam with the desired spot size, including embodiments without diverging beams, and embodiments with converging beams.

The irradiance of the beam at 1 mm from the side of the tip for an 80 W average power laser as described above is about 30 kiloWatts/cm$^2$. According to the present invention, it is desirable to provide a wavelength between about 650 and 200 nm, with a spot size on the surface of the tissue less than about 0.8 mm$^2$, and preferably greater than about 0.05 mm$^2$, with an irradiance greater than about 10 kiloWatts/cm$^2$, and more preferably greater than 20 kiloWatts/cm$^2$, and even more preferably 30 kiloWatts/cm$^2$ or higher.

Figure 12:
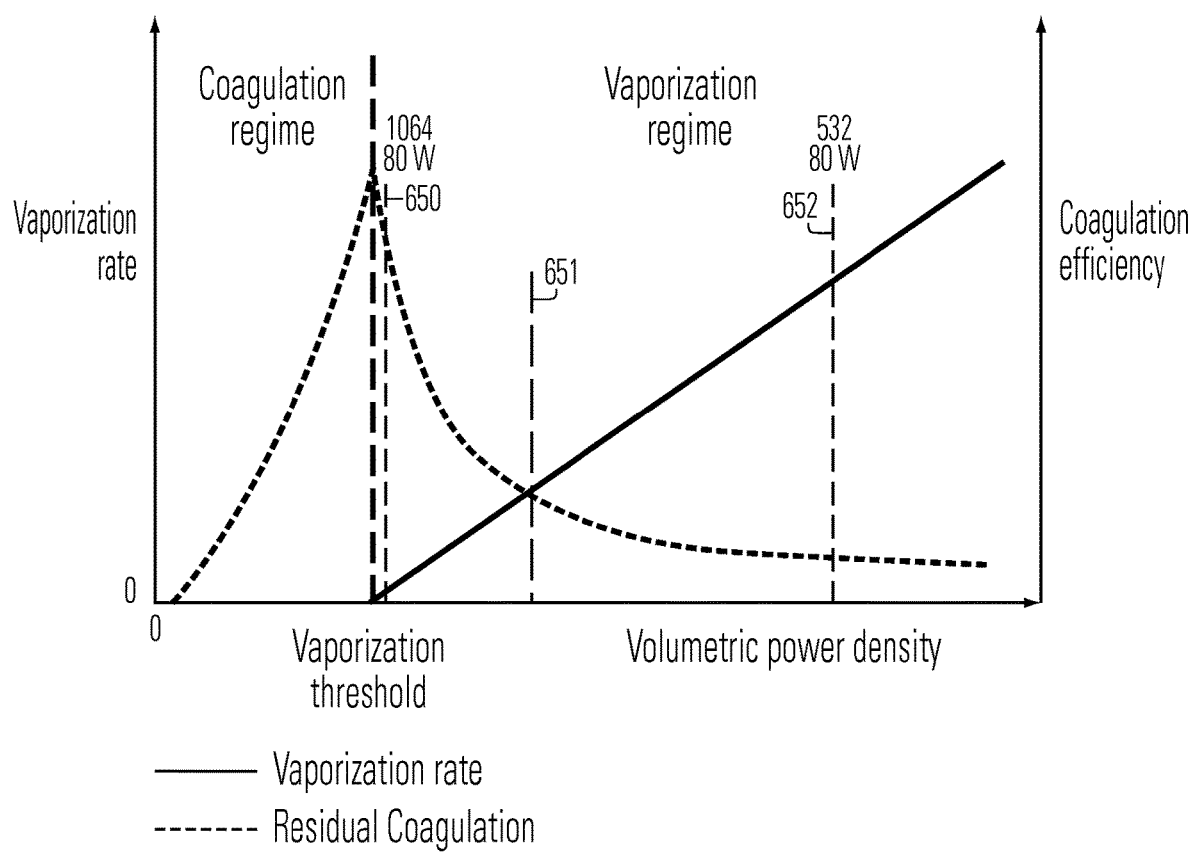
FIG. 12 is a heuristic diagram illustrating operation of the present invention.

FIG. 12 shows, heuristically, how vaporization rate and coagulation rate depend on the volumetric power density. The vaporization rate (in mm/s) is defined as tissue depth that is vaporized per time interval. The coagulation rate (in mm/s) is defined as the depth of residual coagulated tissue that remains after a certain time of vaporization.

Below a certain volumetric power density, referred to as a "vaporization threshold" in FIG. 12, no tissue gets vaporized. All laser energy stays inside the tissue. Tissue coagulation occurs where the tissue temperature rises above approximately 60° C. As the volumetric power density is increased a bigger and bigger tissue volume gets coagulated.

At the vaporization threshold, vaporization starts. Above the vaporization threshold the vaporization rate can be considered to increase linearly with the volumetric power density for the purpose of understanding the present invention, and as described by a steady state model for continuous wave laser tissue ablation, known by those familiar with the art of laser-tissue interaction.

As more and more laser energy is consumed by vaporization of the tissue, the amount of laser energy leading to residual tissue coagulation gets smaller, i.e. the amount of residual coagulation drops. Thus, extent of the zone of thermal damage characterized by tissue coagulation left after the procedure gets smaller with increasing volumetric power density, while the rate of vaporization increases. Substantial and surprising improvement in results is achieved.

Publications about visual laser ablation of the prostate (VLAP) that is performed with an Nd:YAG laser at 1064 nm have shown that this type of laser is not able to vaporize a significant amount of tissue. Histology studies have shown that the 1064 nm laser induces deep coagulation in the tissue that results in edema and delayed tissue sloughing. This effect was described by Kuntzman, et al., *High-power potassium titanyl phosphate laser vaporization prostatectomy*. Mayo Clin Proc 1998:73:798-801. Thus, in the heuristic diagram of FIG. 12, the VLAP procedure is believed to lie around point 650, barely above the vaporization threshold. Also, prior art technologies using 532 nm with spot sizes on the order of 1 mm$^2$ with average output power of 60 Watts, are believed to lie, heuristically, around point 651 in the FIG. 12. Kuntzman et al present results for the coagulation depth of a 60 W continuous wave 532 nm laser, with suggested operation at a distance of 2 mm from the side of the tip, yielding less than 5 kiloWatts/cm$^2$ irradiance.

As the laser power is further increased to 80 W, and the side firing probe is placed less than 1 mm from the tissue for a small spot size, the ablation rate further increases and the coagulation rate further drops, so that the procedure lies heuristically at point 652 in FIG. 12.

An 80 Watt KTP laser can used to easily reach irradiance levels that vaporize substantially more tissue than is left as residual coagulation after the procedure. More precisely, the vaporization rate is substantially higher than the coagulation rate as given by the definition above, using high irradiance levels that are easily achieved with higher power lasers.

While the invention has been particularly shown and described with reference to preferred embodiments thereof, it will be understood by those skilled in the art, that various changes in form and details may be made therein without departing from the spirit and scope of the invention, as defined by the appended claims.

What is claimed is:

1. An apparatus, comprising:
    a solid-state laser capable of producing laser radiation, wherein the laser comprises a laser element assembly, a pump source, a Lithium Triborate frequency doubling crystal, and a controller, wherein:
        the laser element assembly is configured to output 1064 nm light toward the Lithium Triborate frequency doubling crystal to produce second harmonic 532 nm light; and
        the controller is configured to cause the laser to generate, in a macro-pulse mode, a plurality of macro-pulses, each macro-pulse comprising a train of 2 to 12,200 micro-pulses, each micro-pulse being less than one microsecond in duration separated by 40 microseconds from adjacent micro-pulses;
    an optical fiber coupled to the laser and adapted to deliver laser radiation,
    one or more first mirrors configured to direct light from the laser element assembly toward the Lithium Triborate frequency doubling crystal, wherein the one or more first mirrors reflect both 1064 nm and 532 nm light;
    a second mirror that reflects 1064 nm light and is transparent to 532 nm light, wherein the second mirror forms an output window through which the 532 nm light passes through; and
    a user interface comprising a touch screen and a control knob, the user interface being configured to:
        display an average power setting on the screen;
        display a parameter box on the screen; and
        adjust a parameter of the laser when a user touches the parameter box on the screen and then turns the knob.

2. The apparatus of claim 1, wherein each macro-pulse has a peak power greater than 200 watts.

3. The apparatus of claim 1, further including a probe tip including a reflective element disposed within the probe tip that deflects light 40 to 120 degrees relative to a longitudinal axis of the optical fiber, wherein the probe tip includes a transparent window through which the deflected light passes through.

4. The apparatus of claim 1, wherein the laser further includes a Q-switch coupled to the controller, wherein the controller is configured to operate the Q-switch to cause the laser to generate the train of micro-pulses.

5. A laser system comprising:
    a laser configured to generate laser radiation, wherein the laser comprises a Lithium Triborate frequency doubling crystal, and a controller configured to cause the laser to generate, in a macro-pulse mode, a plurality of macro-pulses, each macro-pulse comprising a train of 2 to 12,200 micro-pulses, each micro-pulse being less than one microsecond in duration separated by 40 microseconds from adjacent micro-pulses; and
    an optical fiber.

6. The laser system of claim 5, wherein the optical fiber includes a side firing tip.

7. The laser system of claim 5, further including a probe tip including a reflective element disposed within the probe tip that deflects light 40 to 120 degrees relative to a longitudinal axis of the optical fiber, wherein the probe tip includes a transparent window through which the deflected light passes through.

8. The laser system of claim 5, further including a user interface comprising a touch screen and a control knob, the user interface being configured to:
    display an average power setting on the screen;
    display a parameter box on the screen; and
    adjust a parameter of the laser when a user touches the parameter box on the screen and then turns the knob.

9. The laser system of claim 5, wherein the laser further includes a Q-switch coupled to the controller, wherein the controller is configured to operate the Q-switch to cause the laser to generate the train of micro-pulses.

10. An apparatus, comprising:
    a laser configured to produce laser radiation, wherein the laser comprises a laser element assembly, a frequency doubling crystal, and a controller, wherein the laser element assembly is configured to output light of a first wavelength toward the frequency doubling crystal to produce light of a second wavelength, the first wavelength being double the second wavelength, and the controller is configured to cause the laser to generate, in a macro-pulse mode, a plurality of macro-pulses, each macro-pulse comprising a train of 2 to 12,200 micro-pulses, each micro-pulse being less than one microsecond in duration separated by 40 microseconds from adjacent micro-pulses;

an optical fiber coupled to the laser and adapted to direct laser radiation from the laser to a treatment area on a tissue, one or more first mirrors configured to direct light from the laser element assembly toward the frequency doubling crystal, wherein the one or more first mirrors reflect light of the first wavelength and of the second wavelength; and a second mirror that reflects light of the first wavelength and is transparent to light of the second wavelength, wherein the second mirror forms an output window through which light of the second wavelength passes through; and wherein the laser comprises a Neodymium doped solid state laser medium with greater than 60 watts average output power.

11. The apparatus of claim 10, wherein the optical fiber includes a side firing tip.

12. The apparatus of claim 10, wherein the frequency doubling crystal is a Lithium Triborate frequency doubling crystal.

13. The apparatus of claim 10, wherein the first wavelength is 1064 nm and the second wavelength is 532 nm.

14. The apparatus of claim 10, wherein the laser and optical fiber are configured to deliver an average irradiance of at least 10 kilowatts/cm$^2$ in the treatment area.

15. The apparatus of claim 10, wherein the laser and optical fiber are configured to deliver an average irradiance of at least 20 kilowatts/cm$^2$ in the treatment area.

16. The apparatus of claim 10, wherein the laser and optical fiber are configured to deliver an average irradiance of at least 30 kilowatts/cm$^2$ in the treatment area.

17. The apparatus of claim 10, wherein the laser and optical fiber are configured to deliver an average irradiance in the treatment area greater than 10 kilowatts/cm$^2$ in a spot size of 0.05 mm$^2$.

18. The apparatus of claim 10, wherein the laser and optical fiber are configured to deliver an average irradiance in the treatment area greater than 10 kilowatts/cm$^2$ in a spot size of less than 0.8 mm$^2$.

19. The apparatus of claim 10, wherein the laser further includes a Q-switch coupled to the controller, wherein the controller is configured to operate the Q-switch to cause the laser to generate the train of micro-pulses.

* * * * *